(12) United States Patent
Howard (10) Patent No.: US 7,244,239 B2
(45) Date of Patent: Jul. 17, 2007

(54) SHOULDER STABILIZING RESTRAINT

(75) Inventor: Mark E. Howard, San Diego, CA (US)

(73) Assignee: Breg, Inc., Vista, CA (US)

( * ) Notice: Subject to any disclaimer, the term of this patent is extended or adjusted under 35 U.S.C. 154(b) by 266 days.

(21) Appl. No.: 10/860,963

(22) Filed: Jun. 4, 2004

(65) Prior Publication Data

US 2005/0273026 A1 Dec. 8, 2005

(51) Int. Cl.
*A61F 5/00* (2006.01)
*A61F 5/37* (2006.01)

(52) U.S. Cl. ................. 602/4; 602/5; 602/12; 602/20; 128/878

(58) Field of Classification Search ........... 602/4–6, 602/19, 20, 21, 12, 13, 15, 16, 60–62, 64, 602/77; 128/874, 875, 876, 878–881, 869; 5/646–647; 224/158, 625, 637, 648, 660, 224/662
See application file for complete search history.

(56) References Cited

U.S. PATENT DOCUMENTS

| | | | | |
|---|---|---|---|---|
| RE30,444 E | 12/1980 | Spann | ............ | 128/80 |
| 4,598,701 A | 7/1986 | Schaefer | ............ | 128/87 |
| 4,836,195 A | 6/1989 | Berrehail | ............ | 128/83 |
| 4,896,660 A * | 1/1990 | Scott | ............ | 602/20 |
| 5,060,638 A * | 10/1991 | Bodine, Jr. | ............ | 602/21 |
| 5,334,132 A * | 8/1994 | Burkhead | ............ | 602/4 |
| 5,385,536 A | 1/1995 | Burkhead et al. | ............ | 602/20 |
| 5,464,383 A * | 11/1995 | Padden et al. | ............ | 602/20 |
| 5,569,172 A * | 10/1996 | Padden et al. | ............ | 602/20 |
| 5,665,058 A | 9/1997 | Young | ............ | 602/20 |
| D396,291 S | 7/1998 | Bakes | ............ | D24/190 |
| 6,659,971 B2 * | 12/2003 | Gaylord | ............ | 602/4 |
| 6,932,781 B2 * | 8/2005 | Itoi | ............ | 602/20 |
| 2003/0187373 A1 * | 10/2003 | Gaylord | ............ | 602/4 |
| 2005/0010147 A1 | 1/2005 | Kazmierczak et al. | | |

* cited by examiner

*Primary Examiner*—Patricia Bianco
*Assistant Examiner*—Kiandra C. Lewis
(74) *Attorney, Agent, or Firm*—Rodney F. Brown (57) ABSTRACT

A shoulder stabilizing restraint which includes a pillow and a forearm wrap. The pillow has an arcuately-configured posterior face for engaging an anterior quadrant of a torso on a first side of a user. The pillow also has a flat forearm engagement face for engaging a forearm on the first side of the user. The forearm engagement face is preferably converges with the posterior face at a posterior/lateral convergence which is positionable proximal to a lateral border of the torso on the first side of the user. The forearm wrap is fastenable to the pillow to retain the forearm in engagement with the forearm engagement face and the shoulder joint at a positive external rotation angle.

13 Claims, 8 Drawing Sheets

SHOULDER STABILIZING RESTRAINT

TECHNICAL FIELD

The present invention relates generally to therapeutic stabilization of the shoulder joint, and more particularly to an apparatus for maintaining the shoulder joint in a stable position which facilitates healing of the shoulder joint following an injury or surgery to the joint.

BACKGROUND OF THE INVENTION

Figure 1:
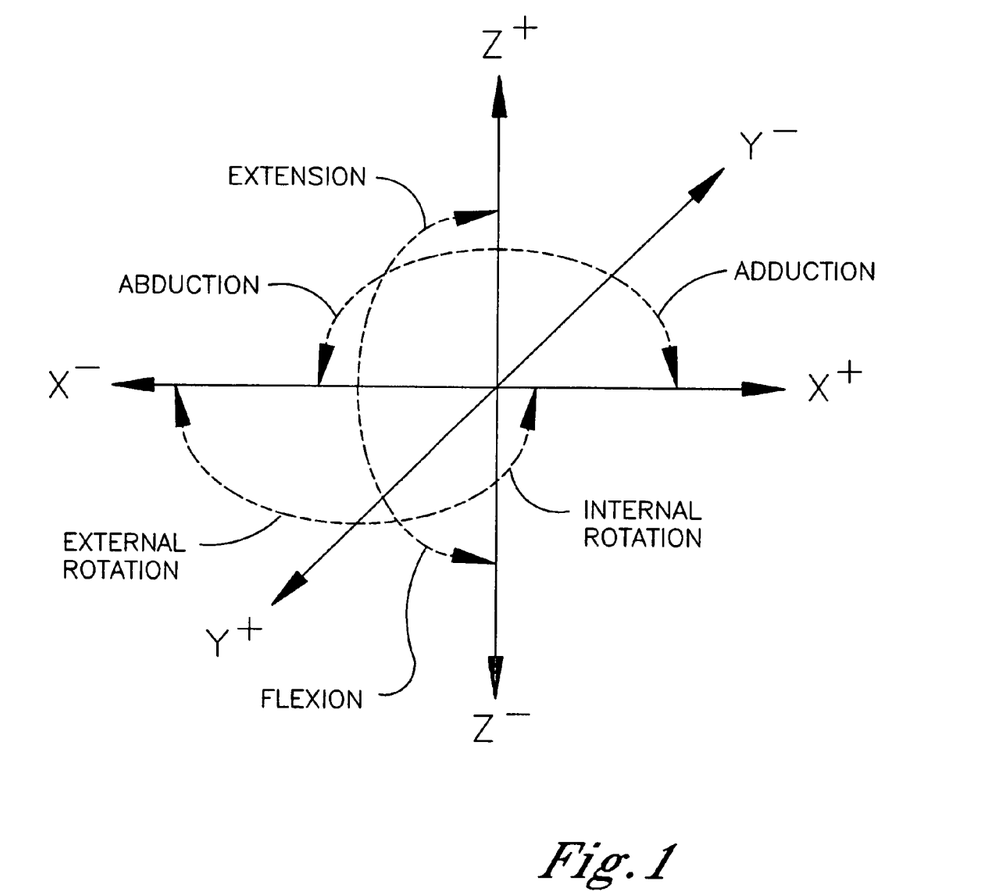
FIG. 1 is a graphical representation of the planes of rotation of a shoulder joint.

The shoulder is a relatively complex joint of the body, which is capable of rotation within multiple planes when the arm is displaced relative to the torso. Referring to FIG. 1, the shoulder is rotatable within three different planes of rotation, i.e., an X-Y plane containing the X and Y axes, an X-Z plane containing the X and Z axes, and a Y-Z plane containing the Y and Z axes. The Z axis has a vertical orientation aligning the Z axis in correspondence with the central longitudinal axis of a standing person. The X and Y axes both have a horizontal orientation, being perpendicular to one another and to the Z axis.

When the Z axis corresponds identically to the central longitudinal axis of a person, the X-Z plane extends longitudinally from right to left through the body of the person when standing and bisects the body into a front or anterior half $Y^+$ and a rear or posterior half $Y^-$, wherein the front half $Y^+$ is forward of the X-Z plane and the rear half $Y^-$ is rearward of the X-Z plane. The Y-Z plane extends longitudinally from front to rear through the body of the person and bisects the body into a right half $X^-$ and a left half $X^+$, wherein the right half $X^-$ is to the right side of the Y-Z plane and the left half $X^+$ is to the left side of the Y-Z plane. The X-Z and Y-Z planes in combination divide the body into four quadrants, i.e., a right anterior quadrant $X^-Y^+$, a left anterior quadrant $X^+Y^+$, a right rear quadrant $X^-Y^-$, and a left rear quadrant $X^+Y^-$. The X-Y plane extends along a latitudinal cross-section of the body aligned in correspondence with the waistline of the body of the person, which bisects the body into an upper half $Z^+$ and a lower half $Z^-$, wherein the upper half $Z^+$ is above the X-Y plane and the lower half $Z^-$ is below the X-Y plane.

Shoulder rotation is termed "external rotation" when the forearm (with the elbow flexed at about 90°) is displaced away from the anterior torso in the X-Y plane. Conversely, shoulder rotation is termed "internal rotation" when the forearm is displaced toward the anterior torso in the X-Y plane. The shoulder and associated arm are said to be at 0° external rotation (or full internal rotation) when the forearm engages or is immediately adjacent to the anterior torso. The degree of external rotation increases as the forearm swings away from the anterior torso to a maximum angle of about 180°. It is noted that the elbow and upper arm of the associated arm can remain in contact with the lateral border of the torso as the shoulder moves through external or internal rotation.

Shoulder rotation is termed "abduction" when the upper arm (independent of the condition of the elbow) is displaced away from the lateral border of the torso in the X-Z plane. Conversely, shoulder rotation is termed "abduction" when the upper arm (independent of the condition of the elbow) is displaced toward the lateral border of the torso in the X-Z plane. The shoulder and associated arm are said to be at approximately 0° abduction (or full abduction) when the elbow and upper arm engage or are immediately adjacent to the lateral border of the torso. The degree of abduction increases as the elbow and upper arm swing away from the lateral border of the torso in the X-Z plane to a maximum angle of about 135°.

Shoulder rotation is termed "flexion" when the arm (independent of the condition of the elbow) is displaced toward the anterior torso in the Y-Z plane. Conversely, shoulder rotation is termed "extension" when the arm is displaced away from the anterior torso in the Y-Z plane. The shoulder and associated arm are said to be at approximately 0° extension (or full flexion) when the elbow and upper arm engage or are immediately adjacent to the lateral border of the torso, i.e., when the upper arm is hanging at the side and lies in the X-Z plane. The degree of extension increases as the upper arm swings away from the anterior torso in the Y-Z plane to a maximum angle of about 180°.

Although the rotational capabilities of the shoulder recited above advantageously enhance the function of the joint, the same expansive rotational capabilities also complicate treatment of the shoulder following injury or surgery. Treatment frequently requires determining a desired optimal healing position of the shoulder and associated arm, placement of the shoulder and associated arm in the desired healing position, and immobilization of the shoulder and arm in the desired healing position. Such a recuperative treatment is particularly applicable to soft tissue injuries involving damage to one or more connective shoulder ligaments and furthermore is oftentimes the treatment of choice following any number of surgical procedures, including surgery for recurrent posterior subluxation, rotator cuff surgery, humeral head or shaft fracture correction, and the like. Healing occurs inter alia through diminution of inflammation and/or regeneration of muscle tissues, which is promoted by removing stress from the injured or surgically corrected joint.

Support devices, such as orthopedic braces, rigid casts, slings and the like, are commonly employed to perform the above-recited placement and immobilization function with varying degrees of success. For example, rigid casts, which are typically molded plaster or resin, have traditionally been used as joint immobilizers. The rigid cast may be replaced from time to time as swelling is reduced. However, the disadvantages of rigid casts are well known. Rigid casts are heavy and uncomfortable to wear and are relatively laborious and complex to apply. Rigid casts may also unduly limit the mobility of the patient and cause joint stiffening and muscle atrophy. In addition, wound and skin treatments and bathing must usually be postponed until the rigid cast is removed.

Support devices using synthetic thermoformable materials are lighter and stronger than rigid casts. However, such devices are significantly more complex and costly. The basic stock materials for constructing the devices are relatively expensive and construction of the devices requires molding all of the constituent parts piece by piece from the stock materials while very hot. The resulting constituent parts are then subsequently joined piece by piece again using heat. Adjusting the fit of the device requires cutting off excess material once the device is in place which can produce sharp edges. In addition, such devices, like rigid casts, can only be used once.

Support devices using metal components are likewise costly and are also relatively heavy. In addition the metal components must be made to order and are typically assembled in an articulated configuration necessitating many fasteners, such as screws, nuts, and bolts, which require significant adjustment.

The present invention recognizes a need for a shoulder orthosis, which is simple, light-weight, and relatively inexpensive, yet highly stable for desired post-surgical or post-injury management of the shoulder. Accordingly, it is an object of the present invention to provide an orthosis for an arm and shoulder which effectively immobilizes the arm and shoulder while accurately positioning the shoulder joint to promote healing and curtail pain. More particularly, it is an object of the present invention to provide an orthosis for an arm and shoulder which restrains the arm, elbow joint and shoulder joint in a more stable position than prior art orthoses. It is another object of the present invention to provide an orthosis for an arm and shoulder which will fit the great majority of patients with a single size and which is adaptable for either the left or the right side of the patient. It is another object of the present invention to provide an orthosis for an arm and shoulder which is light-weight and is easily fitted to the patient. These objects and others are accomplished in accordance with the invention described hereafter.

SUMMARY OF THE INVENTION

The present invention is a shoulder stabilizing restraint. The shoulder stabilizing restraint includes a pillow which has a forearm engagement face and a vertically-aligned posterior face. The forearm engagement face has a relatively flat configuration for engaging a forearm on a first side of a user (i.e., either the right or the left side of the user). The posterior face has an arcuate configuration having a length of about 90° or less for engaging an anterior quadrant of a torso on the same first side of the user as the forearm. The forearm engagement face is preferably a lateral face which diverges anteriorly with respect to the posterior face and converges posteriorly therewith at a posterior/lateral convergence. The posterior/lateral convergence is preferably positionable proximal to a lateral border of the torso on the first side of the user such that the posterior face does not extend substantially rearward of the anterior quadrant.

The shoulder stabilizing restraint preferably also includes means for retaining the forearm in engagement with the forearm engagement face. In accordance with one embodiment, the engagement means is a forearm wrap having a fastener for fastening the forearm wrap to the pillow and sized relative to the user so as to at least partially wrap around the forearm and retain the forearm within the forearm wrap. In a preferred embodiment, the forearm wrap has a first edge connectable to the pillow and a second edge connectable to the pillow to provide a forearm passageway between the forearm wrap and forearm engagement face. The forearm wrap has a length and the forearm engagement face has a length and the length of the forearm wrap is preferably equal to at least a majority of the length of the forearm engagement face.

The shoulder stabilizing restraint further preferably includes a waist belt connected to the pillow and a shoulder strap connectable to the pillow. More particularly, the shoulder strap has a first end connected to the pillow and a second end connected to the waist belt or pillow.

In accordance with a preferred embodiment, the pillow has a unitary construction from a cushion material. In addition to the posterior and lateral faces, the pillow also has an anterior face, which in combination with the posterior and lateral faces defines a triangular profile of the pillow. The lateral and anterior faces intersect at a lateral/anterior intersection and the anterior and posterior faces intersect at an anterior/posterior intersection. The pillow further has a horizontally-aligned top face and a horizontally-aligned bottom face. The first end of the shoulder strap is preferably releasably connected to the pillow proximal to the lateral/anterior intersection. More specifically, the shoulder stabilizing restraint additionally includes a first releasable strap connector on the top face of the pillow for releasably connecting the first end of the shoulder strap to the pillow proximal to the lateral/anterior intersection.

The shoulder stabilizing restraint may further include a second releasable strap connector on the bottom face of the pillow proximal to the lateral/anterior intersection for releasably connecting the first end of the shoulder strap to the pillow when the pillow is reversed to engage a forearm on a second opposite side of the user and an anterior quadrant of the torso on the same second side of the user.

The present invention is also a method for restraining a shoulder joint on a first side of a user, wherein the shoulder joint is connected to an arm having an upper arm, an elbow joint, and a forearm. The method includes the steps of providing a pillow having a posterior face and a lateral face, wherein the posterior face and the lateral face diverge anteriorly and converge posteriorly in a convergence angle at a posterior/lateral convergence. The pillow is positioned such that the posterior face engages an anterior quadrant of the torso on the first side of the user and the lateral face engages the forearm. The posterior/lateral convergence is positioned adjacent to the torso on the first side of the user and the position of the pillow is fixed relative to the user, thereby maintaining the forearm in engagement with the lateral face and the shoulder joint at a positive external rotation angle.

In a preferred embodiment the position of the pillow is fixed relative to the user by encircling the torso with a waist belt connected to the pillow. The position of the pillow is alternately or additionally fixed relative to the user by extending a shoulder strap connected to the pillow over a shoulder on an opposite side of the user. The forearm is maintained in engagement with the lateral face by at least partially covering the forearm with a forearm wrap fastened to the pillow.

The present invention will be further understood from the drawings and the following detailed description.

DESCRIPTION OF PREFERRED EMBODIMENTS

Figure 2:
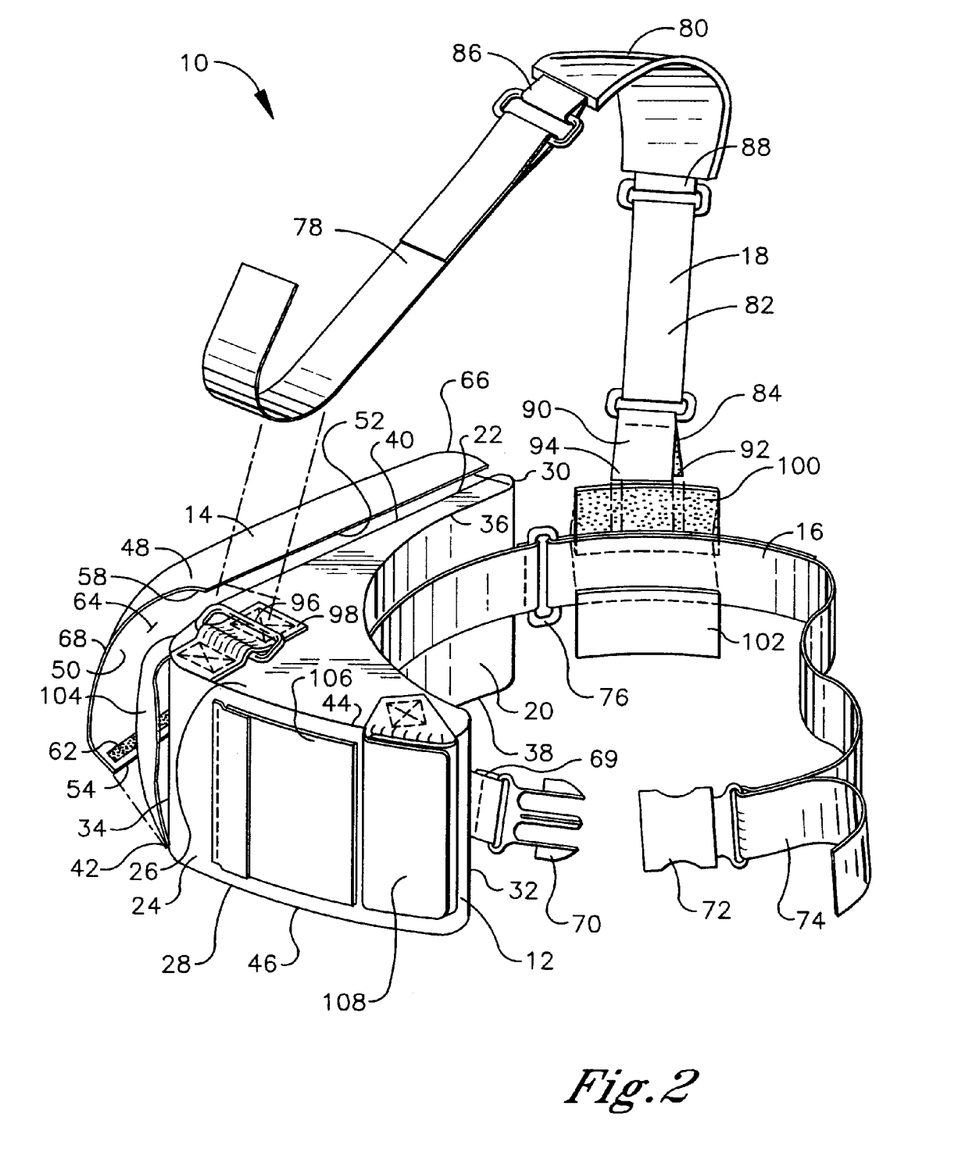
FIG. 2 is a perspective view of a shoulder stabilizing restraint of the present invention.
Figure 3:
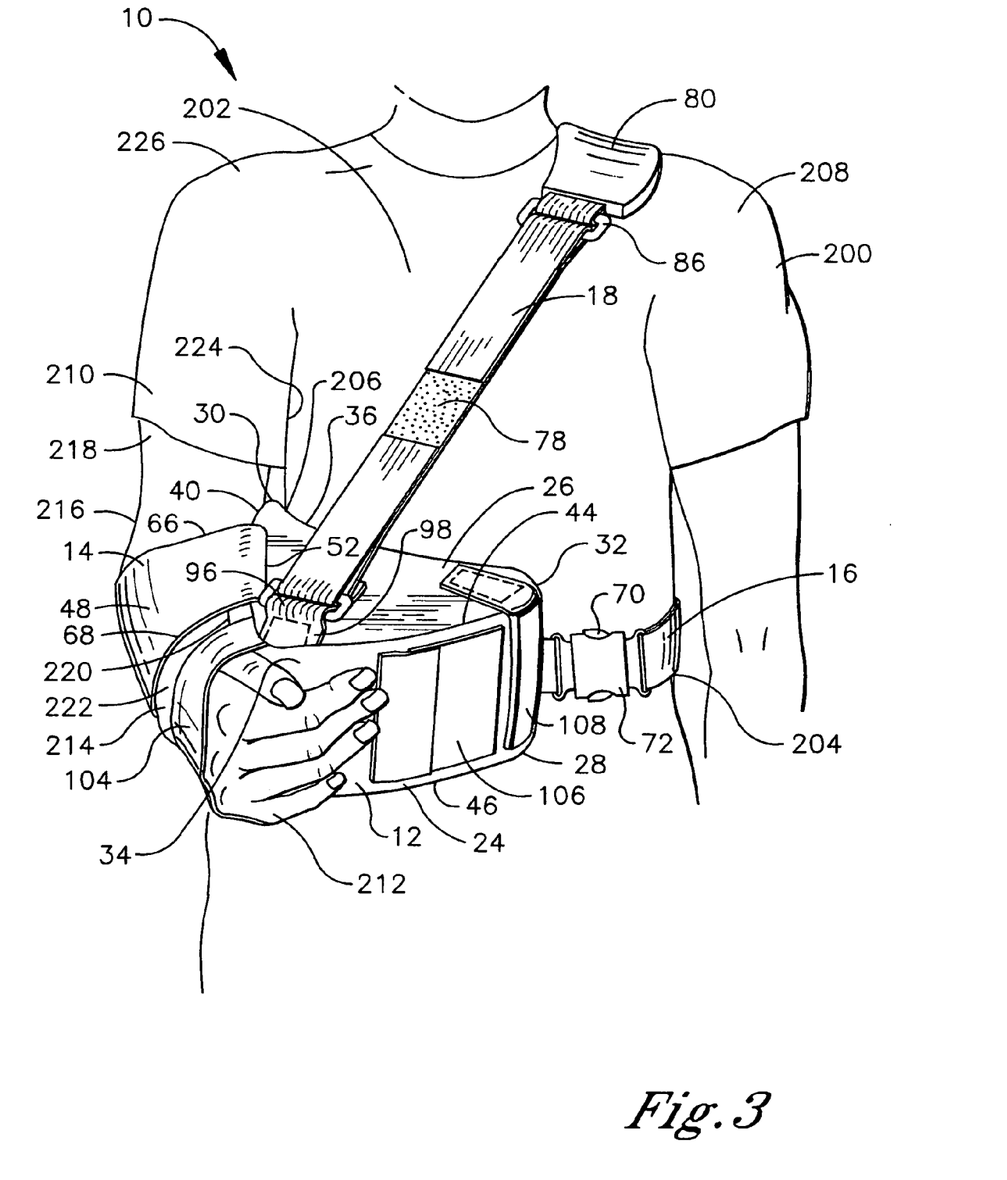
FIG. 3 is an anterior perspective view of the shoulder stabilizing restraint of FIG. 2 operatively mounted on the body of a user.
Figure 4:
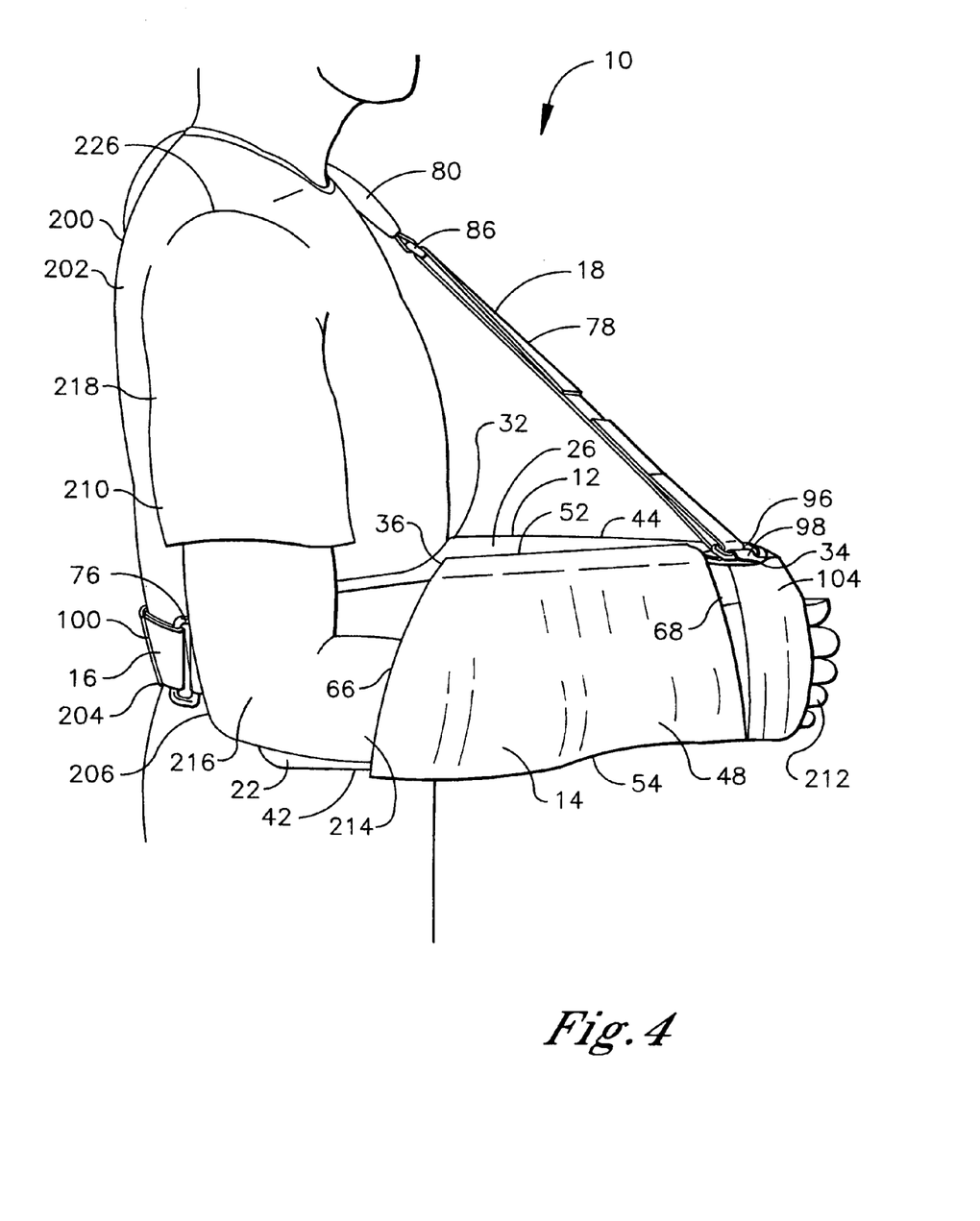
FIG. 4 is a lateral perspective view of the shoulder stabilizing restraint of FIG. 2 operatively mounted on the body of a user.
Figure 5:
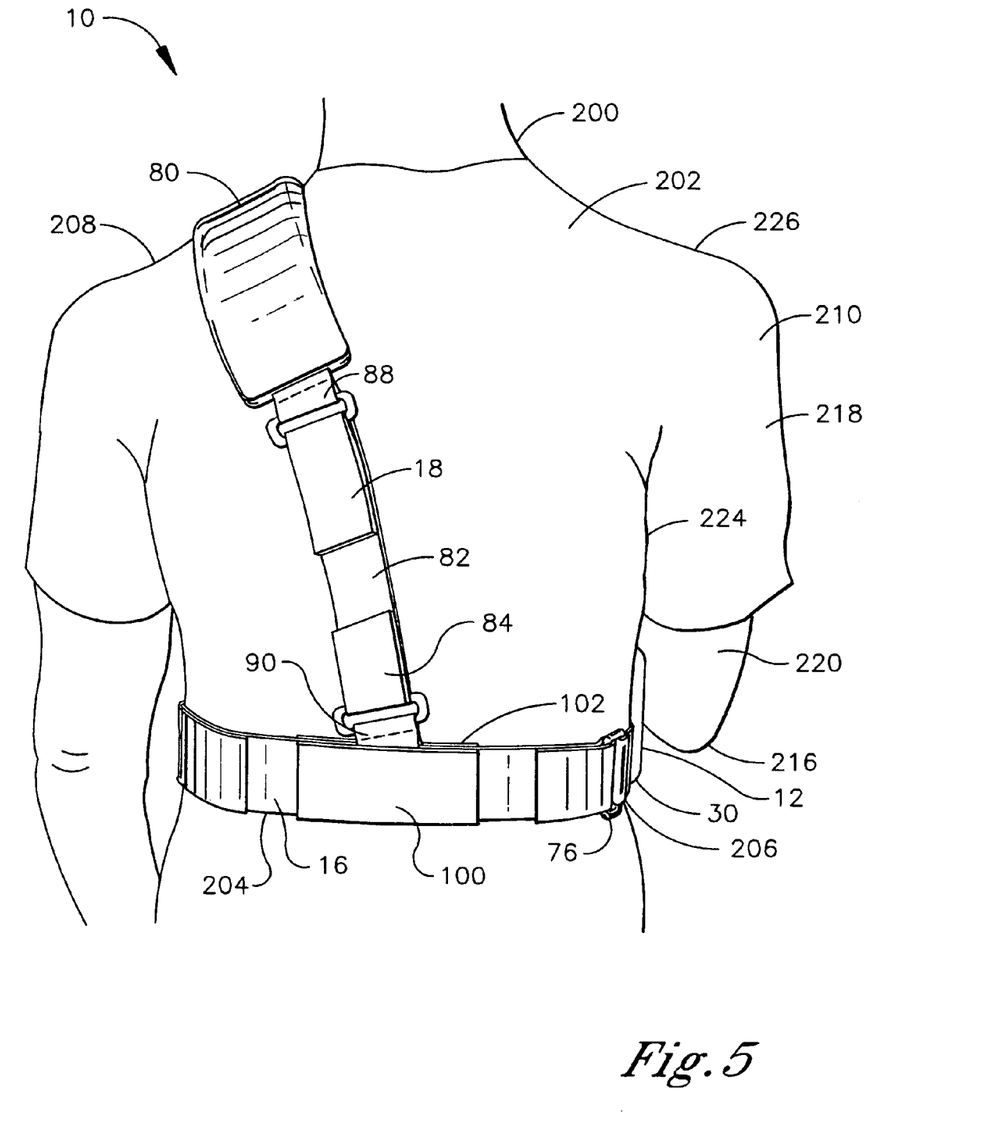
FIG. 5 is a posterior perspective view of the shoulder stabilizing restraint of FIG. 2 operatively mounted on the body of a user.
Figure 6:
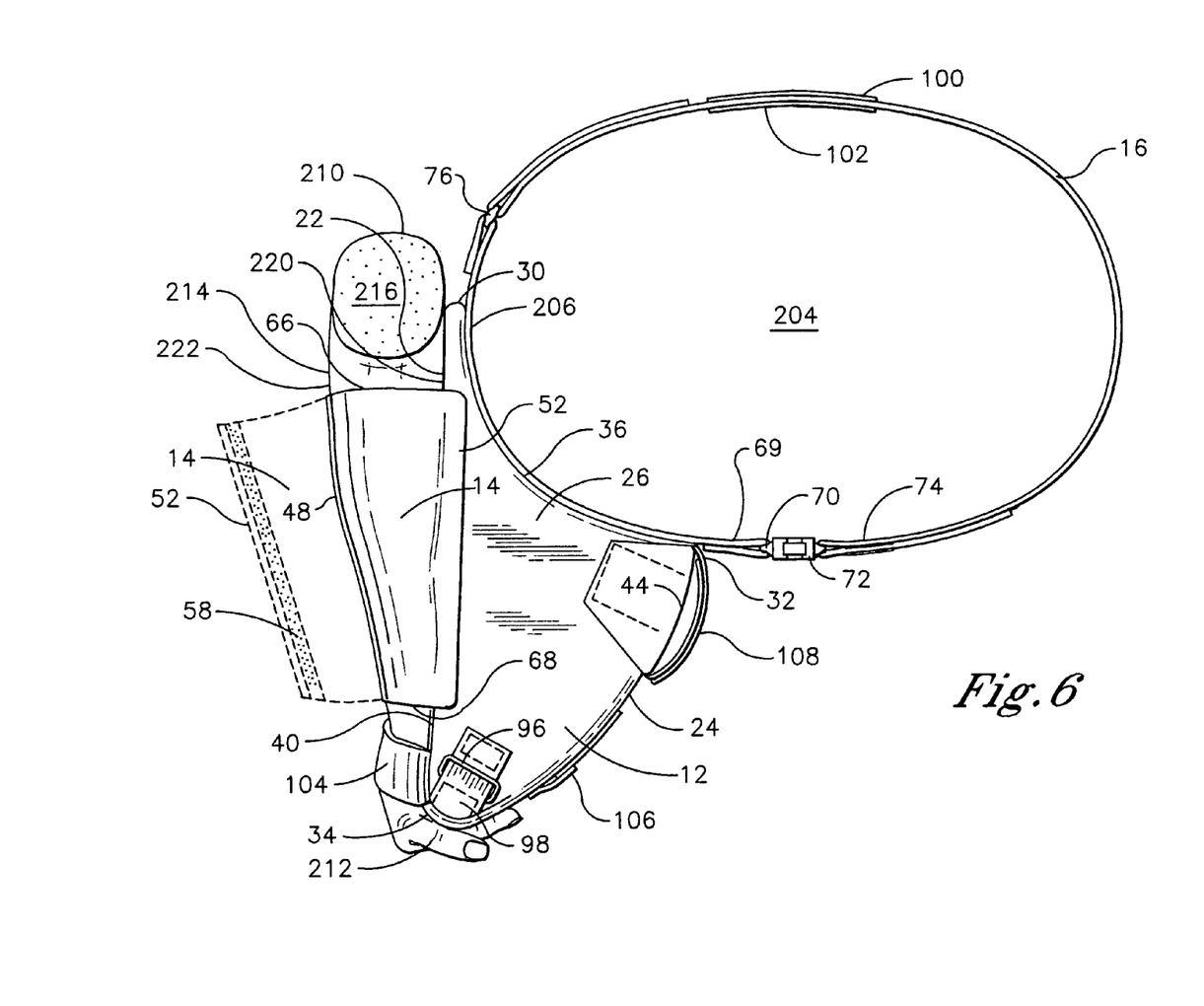
FIG. 6 is a conceptualized top view of the pillow of the shoulder stabilizing restraint of FIG. 2 showing the operative orientation of the pillow relative to the body of a user.

Referring to FIG. 2, an embodiment of a shoulder stabilizing restraint of the present invention is shown and generally designated 10. The shoulder stabilizing restraint 10 of the present embodiment is configured to restrain and stabilize the right shoulder joint of a user. However, the shoulder stabilizing restraint 10 is readily reconfigured to restrain and stabilize the left shoulder joint of a user in a manner described hereafter. A user is defined herein as an individual on whom the shoulder stabilizing restraint 10 is mounted.

The shoulder stabilizing restraint 10 comprises a pillow 12, a forearm wrap 14, a waist belt 16, and a shoulder strap 18. In accordance with the present embodiment, the pillow 12 approximates a triangular profile when viewed from above or below. The pillow 12 has a plurality of faces, which are termed in correspondence with their preferred orientation when the shoulder stabilizing restraint 10 is operatively mounted on a user as described hereafter. In particular, the pillow 12 has three vertically-aligned faces, namely, a posterior face 20, a lateral face 22, and an anterior face 24. The shoulder stabilizing restraint 10 also has two horizontally-aligned faces, namely, a top face 26 and a bottom face 28.

The posterior face 20 has an arcuate profile when viewed from above or below. The arcuate profile enables the posterior face 20 to engage and conform to the curved contour of an anterior quadrant of the torso essentially at or proximal to the waistline of a user when the shoulder stabilizing restraint 10 is operatively mounted in a manner described hereafter. In accordance with the present embodiment, the posterior face 20 is an arc having a length of approximately 90°, i.e., a quarter circle. Although the invention is not limited to a posterior face having an arc of this specific length, the posterior face 20 is, nevertheless, preferably an arc having a length of at least approximately 30° and more preferably an arc having a length of at least approximately 45°. Furthermore, the posterior face 20 is preferably an arc having a length no greater than approximately 180° and more preferably an arc having a length no greater than approximately 135°.

The lateral face 22 is essentially flat, having an essentially straight linear profile when viewed from above or below. The straight profile enables the lateral face 22 to engage and conform to the relatively straight contour of the inside, top, or bottom face of the forearm of a user, when the shoulder stabilizing restraint 10 is operatively mounted on the user.

The posterior and lateral faces 20, 22 converge toward one another in the posterior direction at a posterior/lateral convergence 30, while diverging from one another in the anterior direction. The posterior/lateral convergence 30 is defined hereafter with reference to the lateral border of the torso.

The lateral border of the torso is approximated by the intersection of the X-Z plane with the external surface of the torso of a user when the Z axis is the central longitudinal axis of the torso. When the shoulder is at essentially full flexion, the longitudinal axis of the upper arm aligns with the lateral border of the torso. The posterior/lateral convergence 30 is defined as the rearward terminus of the pillow 12 if the terminus is designed to be positioned at or forward of the lateral border of the torso when the shoulder stabilizing restraint 10 is operatively mounted on a user. However, the posterior/lateral convergence 30 is defined as the portion of the pillow 12 immediately adjacent to the lateral border of the torso (i.e., the portion of the pillow 12 intersecting the X-Z plane), if the rearward terminus of the pillow is designed to be positioned rearward of the lateral border (i.e., rearward of the X-Z plane).

The operative mounting position of the shoulder stabilizing restraint 10 on the user and the configuration of the posterior/lateral convergence 30 determine both the degree of external rotation and the degree of abduction, which is imposed by the shoulder stabilizing restraint 10 on a shoulder joint. The configuration of the posterior/lateral convergence 30 is characterized by two parameters, the convergence angle and the convergence distance. The convergence angle is defined herein as an approximation of the angle between the line of the lateral face 22 and the slope of the arcuate posterior face 20. The convergence distance is defined herein as the linear distance separating the posterior and lateral faces 20, 22 at the posterior/lateral convergence 30.

Although the invention is not limited to any one specific configuration of the posterior/lateral convergence, the posterior/lateral convergence 30 of the present embodiment is configured as a narrowtip, which is designed to be positioned at or near the lateral border of the torso when the shoulder stabilizing restraint 10 is operatively mounted on the user. The posterior and lateral faces 20, 22 essentially intersect at the posterior/lateral convergence 30. Accordingly, the convergence distance of the present embodiment is very small approaching zero and the convergence angle is an acute angle.

A convergence angle of about 15° or more, and preferably from about 20° to about 45° usually results in an effective degree of external rotation of the shoulder joint when the shoulder stabilizing restraint 10 is operatively mounted on a user with the posterior/lateral convergence 30 positioned at or near the lateral border of the torso. In general, the degree of external rotation imposed by the shoulder stabilizing restraint 10 on the shoulder joint is correlated directly to the size of the convergence angle of the posterior/lateral convergence 30. Thus, the degree of external rotation increases as the convergence angle increases and the degree of external rotation decreases as convergence angle decreases.

A convergence distance of about one inch or less usually results in a negligible degree of abduction on the shoulder joint. Such a small convergence distance only slightly separates the elbow from the lateral border of the torso, if at all, when the shoulder stabilizing restraint 10 is operatively mounted on a user with the posterior/lateral convergence 30 positioned at or near the lateral border of the torso. In accordance with an alternate embodiment described hereafter, the convergence distance can be increased substantially over the present embodiment. For example, the posterior and lateral faces 20, 22 can be separated by two or more inches from one another at the posterior/lateral convergence 30. When a shoulder stabilizing restraint is operatively mounted on a user, which has a substantial convergence distance, the shoulder stabilizing restraint can impose a significant degree of abduction on the shoulder joint.

In general, the degree of abduction imposed by the shoulder stabilizing restraint 10 on the shoulder joint is correlated directly to the convergence distance. Thus, the degree of abduction increases when the convergence distance increases and the degree of abduction decreases when the convergence distance decreases.

The anterior face 24 is a connective face between the divergent posterior and lateral faces 20, 22. The anterior face 24 may have a straight profile, an arcuate profile, or an irregular (e.g., multifaceted) profile as desired. The anterior face 24 is essentially free from engagement with the user (with the exception of the fingers as described hereafter) when the shoulder stabilizing restraint 10 is operatively mounted. The intersection angles of the posterior and anterior faces 20, 24 and of the lateral and anterior faces 22, 24, respectively, are preferably substantially greater than the convergence angle of the posterior and lateral faces 20, 22. Accordingly, the posterior and anterior faces 20, 24 and the lateral and anterior faces 22, 24 have intersections 32 and 34, respectively, which are generally more blunted than the present posterior/lateral convergence 30.

The top and bottom faces 26, 28 are preferably flat planar surfaces, which are essentially parallel to one another and are essentially perpendicular to the posterior, lateral and anterior faces 20, 22, 24, respectively. Accordingly, the intersection angles of the posterior and top faces 20, 26, posterior and bottom faces 20, 28, lateral and top faces 22, 26, lateral and bottom faces 22, 28, anterior and top faces 24, 26, and anterior and bottom faces 24, 28, which define intersections 36, 38, 40, 42, 44, 46, respectively, are all essentially right angles. Although the lateral and anterior faces 22, 24 as described above are preferably vertically aligned, it is further within the scope of the present invention to align the flat lateral face 22 and/or the anterior face 24 at an angle with vertical so that the lateral and/or anterior faces 22, 24 do not necessarily intersect the top and bottom faces 26, 28 at right angles. In any case, the top and bottom faces 26, 28 are preferably essentially free from engagement with the torso of the user when the shoulder stabilizing restraint 10 is operatively mounted.

The pillow 12 preferably has a unitary, i.e., one-piece, construction. The pillow 12 is preferably constructed from a cushion material, such as a shaped block of a solid foam. The foam is preferably elastically compressible when subjected to significant external forces, but does not substantially compress when subjected to the normal tension forces applied to the pillow 12 by the arm and shoulder joint of a user when the shoulder stabilizing restraint 10 is operatively mounted on the user. The foam is preferably enclosed within a fabric cover, which performs a number of functions. The fabric cover enhances the comfort of the user where the pillow 12 engages the body of the user. The fabric cover also protects the foam from external abrasion and the like. In addition, the fabric cover provides a surface for attaching supplemental accessories or other utilitarian elements to the pillow 12 as described hereafter. Attachment is typically effected by sewing, hook and loop fastening, or the like.

The forearm wrap 14 is a piece of elastically stretchable fabric having an outside face 48, an inside face 50, and first and second edges 52, 54, which are essentially parallel to and opposite one another. A first fastener 58 extends along the first edge 52. The first fastener 58 is preferably formed from either the hook material or the loop material of a hook and loop fastener, commonly known by the trade name "VELCRO". The hook or loop material is sewn onto the inside face 50 of the forearm wrap 14. In a preferred embodiment, the fabric cover of the pillow 12 is formed from a hook or loop material which compliments the hook or loop material of the first fastener 58. As such, the fabric cover enables releasable hook and loop fastening of the first fastener 58 directly to the top face 26 of the pillow 12 proximal to and aligned with the intersection 40. A first stiffening member (not shown) also extends along the first edge 52 beneath the first fastener 58. The first stiffening member is preferably a stiff plastic or metal bar retained within a pocket sewn into the outside or inside face 48, 50 of the forearm wrap 14.

A second fastener 62 extends along the second edge 54 in the same manner as the first fastener 58. The fabric cover of the pillow 12 likewise functions as a fastener complimentary to the second fastener 62. The fabric cover enables releasable hook and loop fastening of the second fastener 62 directly to the bottom face 28 of the pillow 12 proximal to and aligned with the intersection 42. A second stiffening member (not shown) also extends along the second edge 54 in the same manner as the first stiffening member.

Releasably fastening the forearm wrap 14 to the pillow 12 by means of the first and second fasteners 58, 62, provides an open forearm passageway 64 between the inside face 50 of the forearm wrap 14 and the lateral face 22 of the pillow 12, which extends essentially parallel to the intersections 40 and 42. The forearm passageway 64 is open at third and fourth edges 66, 68 of the forearm wrap 14, which are essentially opposite one another and adjacent to the first and second edges 52, 54. The third and fourth edges 66, 68 are also essentially, but not necessarily precisely, parallel to one another and essentially, but not necessarily precisely, perpendicular to the first and second edges 52, 54. The forearm wrap 14 preferably has a slight taper along the third and fourth edges 66, 68 from the second edge 54 to the first edge 54.

The forearm wrap 14 has a length, i.e., the distance from the third edge 66 to the fourth edge 68, approximately equal to the length of the forearm of a user, i.e., the distance between the elbow and wrist joints of the user. As such, the length of the forearm passageway 64 is approximately equal to the length of the forearm. The length of the forearm passageway 64 and correspondingly the length of the forearm wrap 14 are somewhat less than length of the lateral face 22, i.e., the distance between the intersections 30 and 34, but are preferably equal to at least a majority of the length of the lateral face 22.

Although only a single embodiment of a means for retaining the forearm of a user in engagement with the lateral face 22 of the pillow 12 is shown and described herein, i.e., the forearm wrap 14, it is apparent that there are any number of alternate constructions of forearm retention means, which achieve the same or a similar result. Such alternate constructions are within the purview of the skilled artisan and, as such, are within the scope of the present invention.

The waist belt 16 is preferably formed from a flexible fabric, which is essentially non-stretchable. In accordance with the present embodiment, the waist belt 16 comprises a first segment 69 fixably attached to the pillow 12 along the length of the posterior face 20 by sewing the first segment 69 directly to the fabric cover of the pillow 12. A conventional releasable male coupler 70 is fixably attached to the first segment 69 of the waist belt 16 proximal to the intersection 32 by threading the first segment 69 through the male coupler 70, doubling the first segment back onto itself, and fixably attaching the first segment 69 to itself, preferably by sewing. A conventional releasable female coupler 72 is provided on a second segment 74 of the waist belt 16, which compliments the releasable male coupler 70, and a adjustment loop 76 is provided in the waist belt 16, which adjustably joins the first and second segments 69, 74 of the waist belt 16 at ends opposite the couplers 70, 72. The couplers 70, 72 enable releasable closure of the waist belt 16 to form a continuous closed-loop path and the adjustment loop 76, in cooperation with the female coupler 72, enables the user to adjust the length of the closed-loop path of the waist belt 16 in a manner within the purview of the skilled artisan, so that the shoulder stabilizing restraint 10 can be adapted to different size users.

The shoulder strap 18 of the present embodiment likewise comprises a plurality of segments. Specifically, the shoulder strap 18 has four segments, namely, an anterior segment 78, a shoulder segment 80, a posterior segment 82, and a connective segment 84. The anterior and posterior segments 78, 82 are essentially identical lengths of a flexible non-stretchable fabric, which is preferably the same or similar to the material of the waist belt 16. The shoulder segment 80 is constructed from a flexible non-stretchable cloth-covered foam having an arcuate configuration, which enables the shoulder segment 80 to engage and conform to the curved contour of the shoulder without pinching the neck of a user when the shoulder stabilizing restraint 10 is operatively mounted. The shoulder segment 80 is provided with first and second connective loops 86, 88 which are fixably attached to opposite ends of the shoulder segment 80.

The connective segment 84 is a length of flexible non-stretchable fabric, which is threaded through and fixably attached to a connective loop 90. First and second opposite ends 92, 94 of the connective segment 84 are free-hanging and extend away from the connective loop 90. The fabric of the connective segment 84 is preferably either the hook material or the loop material of a hook and loop fastener.

The shoulder strap 18 is assembled by threading an end of the anterior segment 78 through the first connective loop 86 of the shoulder segment 80, doubling the threaded end back onto the anterior segment 78, and releasably fastening the end to the anterior segment 78, preferably by hook and loop fastening, thereby releasably connecting the anterior segment 78 to the shoulder segment 80. The posterior segment 82 is similarly releasably connected to the shoulder segment 80 by means of the second connective loop 88. The posterior segment 82 is also releasably connected to the connective segment 84 by threading the opposite end of the posterior segment 82 through the connective loop 90 of the connective segment 84, doubling the threaded end back onto the posterior segment 82, and releasably fastening the end to the posterior segment 82, preferably by hook and loop fastening. The length of the shoulder strap 18 is adjustable by repositioning the fastening point of the end of the anterior segment 78 and/or the end of the posterior segment 82 in a manner within the purview of the skilled artisan, so that the shoulder stabilizing restraint 10 can be adapted to different size users.

Although only a single embodiment of the shoulder strap 18 having a four-segment configuration is shown and described above, it is apparent that there are any number of alternate constructions of the shoulder strap, which are within the purview of the skilled artisan and which are within the scope of the present invention. For example, an alternate shoulder strap having utility in the shoulder stabilizing restraint of the present invention can be integrally constructed from a single continuous length of material. Similarly, although only a single embodiment of the waist belt 16 having a two-segment configuration is shown and described above, it is apparent that there are any number of alternate constructions of the waist belt, which are within the purview of the skilled artisan and which are within the scope of the present invention. For example, an alternate waist belt having utility in the shoulder stabilizing restraint of the present invention can be integrally constructed from a single continuous length of material.

In any case, a first pillow connective loop 96 is provided on the pillow 12, which enables releasable connection of the shoulder strap 18 to the pillow 12. The first pillow connective loop 96 is fixably attached to the top face 26 of the pillow 12 proximal to the lateral/anterior intersection 34, preferably by threading an attachment strip 98 formed from a fabric through the first pillow connective loop 96 and sewing the ends of the attachment strip 98 to the cloth cover of the pillow 12. The shoulder strap 18 is releasably connected to the pillow 12 by threading an end of the anterior segment 78 through the first pillow connective loop 96, doubling the threaded end back onto the anterior segment 78, and releasably fastening the end to the anterior segment 78, preferably by hook and loop fastening. An essentially identical second pillow connective loop (not shown) is preferably provided on the bottom face 28 of the pillow 12 opposite the first pillow connective loop 96, which enables the shoulder stabilizing restraint 10 to be alternately configured for the left shoulder joint of a user in a manner described hereafter.

The shoulder strap 18 is releasably connected to the waist belt 16 by means of the connective segment 84. In the present embodiment, the fabric of the waist belt 16 is preferably the hook or loop material which compliments the hook or loop material of the connective segment 84. Accordingly, the inside face of the first end 92 of the connective segment 84 is releasably fastened by hook and loop fastening to the outside face of the waist belt 16, while the inside face of the second end 94 of the connective segment 84 is releasably fastened by hook and loop fastening to the inside face of the waist belt 16. A fabric outside securing strip 100 is optionally releasably fastened, preferably by hook and loop fastening, to the outside face of the waist belt 16 over the first end 92 of the connective segment 84, which further secures the releasable connection of the first end 92 to the waist belt 16. A fabric inside securing strip 102 is similarly optionally releasably fastened, preferably by hook and loop fastening, to the inside face of the waist belt 16 over the second end 94 of the connective segment 84, which further secures the releasable connection of the second end 94 to the waist belt 16.

In accordance with an alternate embodiment not shown, the connective segment can be alternatively configured to enable connection of the respective end of the shoulder strap 18 to the pillow 12, rather than to the waist belt 16 as shown and described herein. For example, it is within the purview of the skilled artisan to configure the connective segment in a manner which enables connection of the respective end of the shoulder strap 18 to the pillow 12 at or proximal to the posterior/lateral convergence 30 without departing from the scope of the present invention.

The shoulder stabilizing restraint 10 preferably further comprises a hand support loop 104 vertically aligned across the lateral face 22 of the pillow 12 and positioned between the fourth edge 68 of the forearm wrap 14 and the intersection 34. The hand support loop 104 is formed from a length of flexible non-stretchable fabric. One end of the hand support loop 104 is sewn to the cloth covering of the pillow 12 at the intersection 40. The opposite end of the hand support loop 104 is sewn to the cloth covering of the pillow 12 at the intersection 42.

Since the anterior face 24 is essentially free from engagement with the user when the shoulder stabilizing restraint 10 is operatively mounted on a user, the anterior face 24 provides an unobstructed mounting surface for supplemental accessories. In accordance with the present embodiment, a selectively sealable cloth storage pocket 106 is sewn to the cloth covering of the pillow 12 over the anterior face 24. An infusion pump holder 108 is also sewn to the cloth covering of the pillow 12 over the anterior face 24 adjacent to the storage pocket 106 and proximal to the intersection 32. An infusion pump (not shown), such as disclosed in U.S. Pat. No. 6,270,481, may be retained in the infusion pump holder 108 to provide a user of the shoulder stabilizing restraint 10 with a supply of pain medication for the affected shoulder joint.

A method for mounting the shoulder stabilizing restraint 10 on a user 200 and the resulting position of the mounted shoulder stabilizing restraint 10 relative to the body of the user 200 is shown and described hereafter with continuing reference to FIG. 2 and additional reference to FIGS. 3-6. The present mounting method is performed by the user alone or with the assistance of another as needed.

The method is initiated by adjusting the length of the posterior segment 82 of the assembled shoulder strap 18 in accordance with the height and girth of the torso 202, respectively, of the user 200. The connective segment 84 is releasably fastened to the waist belt 16 in the manner described above and the second fastener 62 of the forearm wrap 14 is releasably fastened to the bottom face 28 of the pillow 12. If desired, the outside and inside securing strips 100, 102 are also releasably fastened to the waist belt 16 over the connective segment 84.

The pillow 12 is positioned on the torso 202 of the user at or proximal to the waistline 204 with the couplers 70, 72 of the waist belt 16 uncoupled and the forearm wrap 14 and shoulder strap 18 partially connected to the pillow 12 as described above. The posterior face 20 of the pillow 12 is fitted in essentially continuous engagement with the right anterior quadrant of the torso 202 and does not substantially extend past the right anterior quadrant of the torso 202 in either direction. As such, the posterior/lateral convergence 30 of the pillow rests adjacent to the right lateral border 206 of the torso 202. In accordance with the present embodiment, the plane of the lateral face 22 is also in approximate perpendicular alignment with the X-Z plane. The shoulder strap 18 is draped over the left shoulder 208 of the user 200 with the shoulder segment 80 engaging the left shoulder 208 and the anterior segment 78 extending toward the first pillow connective loop 96.

The right arm 210 of the user 200, which comprises a right hand 212, a right forearm 214, a right elbow joint 216, and a right upper arm 218, is positioned as follows relative to the pillow 12 and torso 202. The right hand 210 is slipped through the hand support loop 104 with the palm of the right hand 210 engaging the intersection 34 of the pillow 12 and the back of the right hand 210 engaging the hand support loop 104. If desired, the fingers of the right hand 210 may be curled around the intersection 34 to engage a small portion of the anterior face 24 of the pillow 12. The right forearm 214 has an inside face 220 and an outside face 222 and the right forearm 214 is rotated such that the inside face 220 is essentially medially oriented, i.e., the inside face 220 is the face of the right forearm 214 which is most proximal to the central longitudinal axis of the torso 202. As such, the inside face 220 of the right forearm 214 is positioned in essentially continuous engagement with the lateral face 22 of the pillow 12. The right upper arm 218 likewise has an inside face 224, which is positioned in engagement with, or in very close proximity to, the torso 202 proximal to the right lateral border 206 of the torso 202.

The forearm wrap 14 is drawn upward so that the inside face 50 of the forearm wrap 14 engages the laterally-oriented outside face 222 of the right forearm 212, i.e., the outside face 222 is the face of the right forearm 214 which is most distal from the central longitudinal axis of the torso 202. The first fastener 58 of the forearm wrap 14 is releasably fastened to the top face 26 of the pillow 12 retaining the right forearm 214 in the forearm passageway 64 of the forearm wrap 14. The resulting flexion angle of the right elbow joint 216 of the user 200 is about 90° and the external rotation angle of the right shoulder joint 226 of the user is about 90°. This external rotation position of the right arm 210 and the right shoulder joint 226 is termed the "neutral position" because in many cases it minimizes the degree of tension on the affected shoulder joint. Consequently, the neutral position facilitates healing of the injured or otherwise damaged shoulder joint while abating pain in the shoulder joint. It is further noted that the abduction angle of the right shoulder joint 226 of the user 200 is about 0° and the extension angle of the right shoulder joint 226 is likewise at or near 0° in the present embodiment.

Once the right arm 210 and the right shoulder joint 226 are in the neutral position, the couplers 70, 72 of the waist belt 16 are coupled together and the length of the waist belt 16 is adjusted as necessary, in accordance with the girth of the torso 202 at or proximal to the waistline 204, thereby closing the waist belt 16 around the torso 202 of the user 200 in a continuous closed-loop path. Finally, the anterior segment 78 is connected to the pillow 12 by means of the first pillow connective loop 96 in the manner described above. The length of the anterior segment 78 is adjusted such that the top and bottom faces 26, 28 of the pillow 12 are essentially horizontally aligned to complete the present mounting method. The shoulder stabilizing restraint 10 retains the right arm 210 and the right shoulder joint 226 in the neutral position thereafter.

Figure 7:
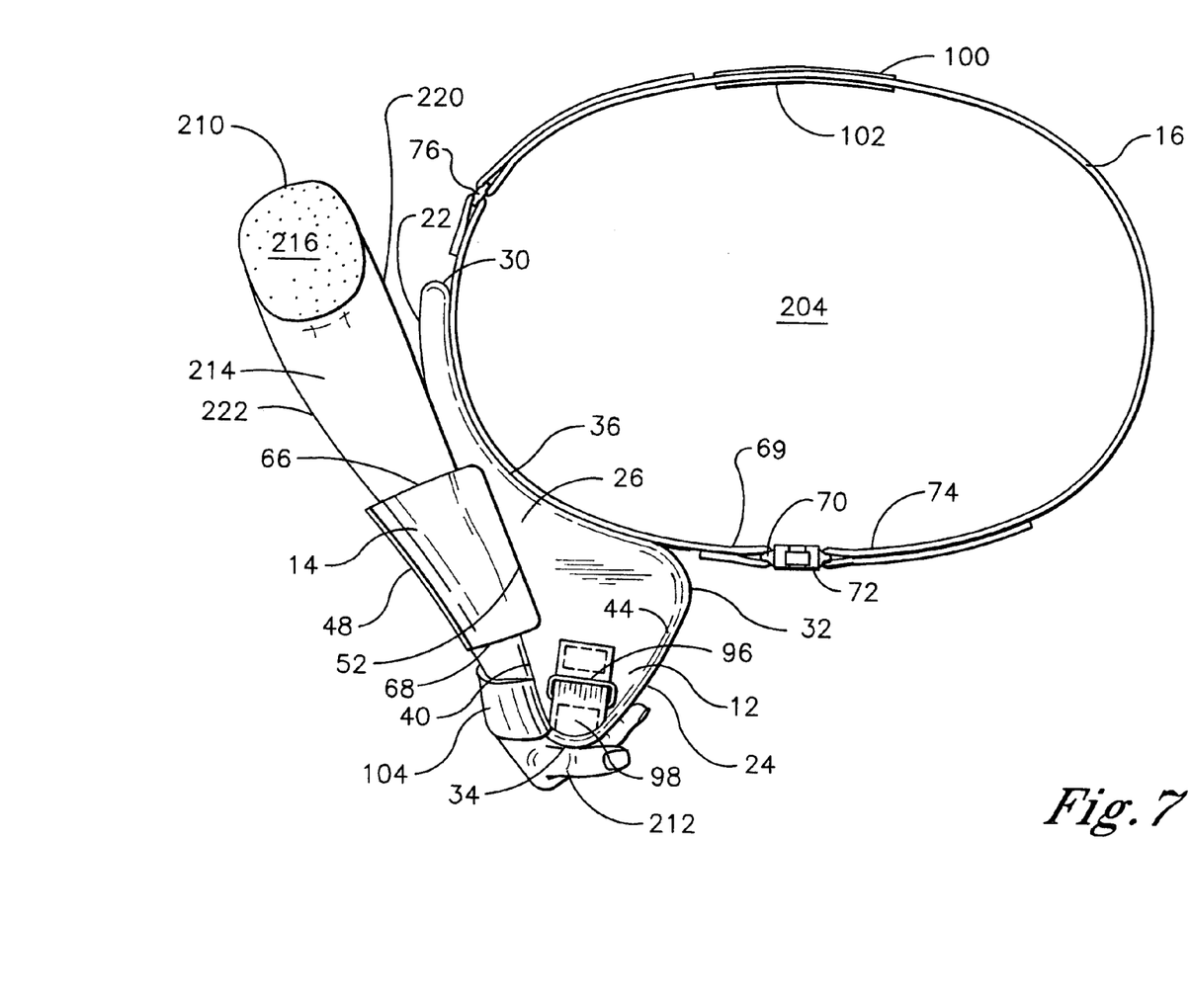
FIG. 7 is a conceptualized top view of an alternate embodiment of the pillow of the shoulder stabilizing restraint of FIG. 2, which shows the operative orientation of the pillow relative to the body of a user, wherein the pillow imposes a smaller degree of external rotation on the shoulder joint than in FIG. 6.

As noted above, the configuration of the pillow 12 can be modified within the scope of the invention to accommodate alternate positions of the right arm 210 and shoulder joint 226, if desired. For example, the pillow 12 can be configured to impose a larger or smaller external rotation angle of the right shoulder joint 226 of the user 200 by changing the convergence angle of the posterior/lateral convergence 30 as described above. FIG. 7 shows the pillow 12 configured to impose a smaller external rotation angle of the right shoulder joint of the user by decreasing the convergence angle. In any case, it is a preferred feature of the present invention that the shoulder stabilizing restraint 10 imposes a positive and substantial external rotation on the right shoulder joint of the user (or the left shoulder joint of the user when the shoulder stabilizing restraint is reconfigured to restrain and stabilize the left shoulder joint in a manner described hereafter). The shoulder stabilizing restraint 10 preferably imposes an external rotation angle of at least about 30°, and more preferably imposes an external rotation angle of at least about 45°.

Figure 8:
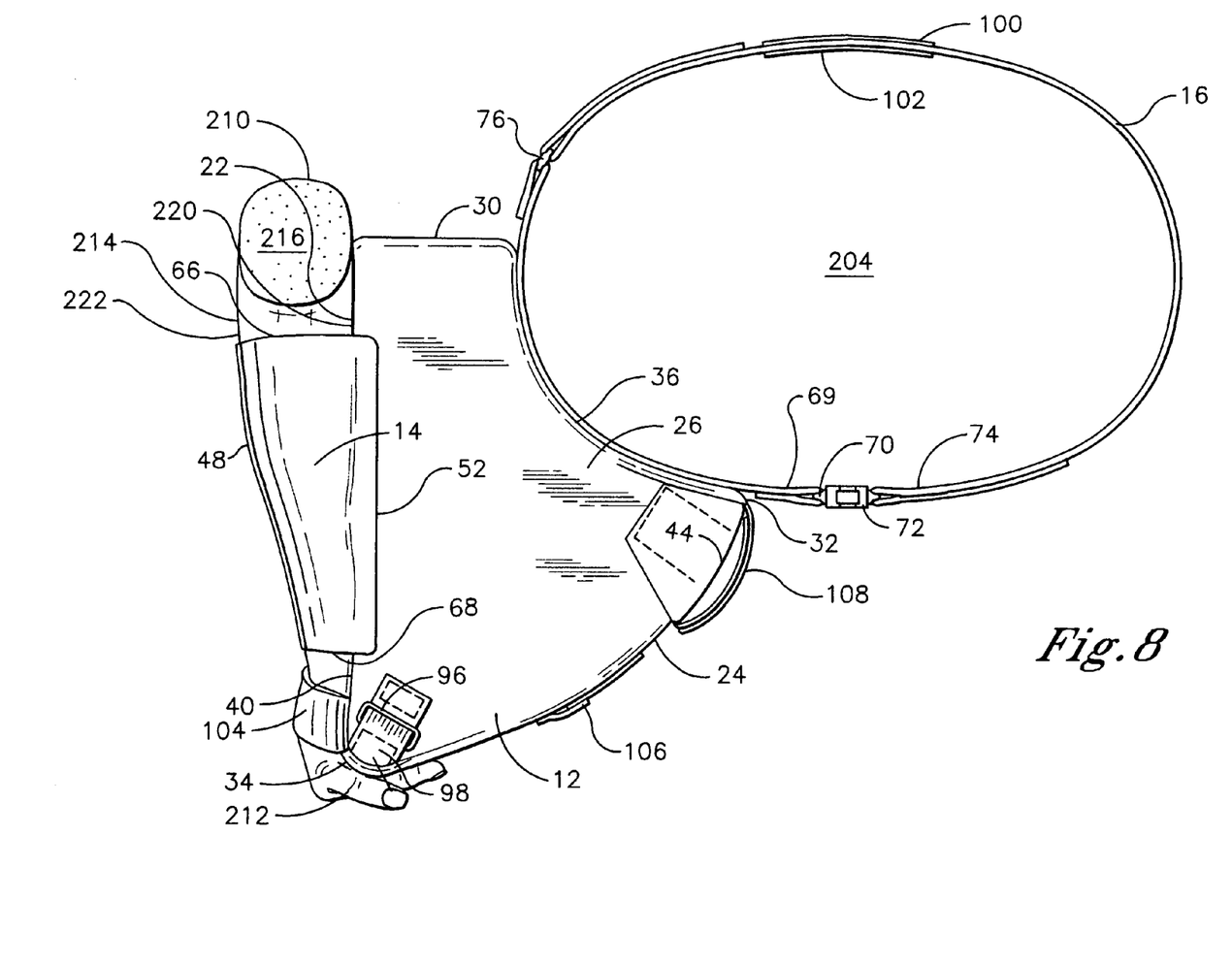
FIG. 8 is a conceptualized top view of an alternate embodiment of the pillow of the shoulder stabilizing restraint of FIG. 2, which shows the operative orientation of the pillow relative to the body of a user, wherein the pillow imposes a greater degree of abduction on the shoulder joint than in FIG. 6.

Additionally or in the alternative, the pillow 12 can be configured to impose a larger abduction angle of the right shoulder joint of the user by increasing the convergence distance of the posterior/lateral convergence 30 as shown in FIG. 8. The shoulder stabilizing restraint 10 preferably imposes an abduction angle between about 0 and 90° and more preferably imposes an abduction angle between about 0 and 45°.

It is another preferred feature of the invention that the posterior/lateral convergence 30 does not substantially extend along the right side of the user 200 posteriorly past the X-Z plane when the shoulder stabilizing restraint 10 is operatively mounted on a user with the posterior/lateral convergence 30 positioned at or near the right lateral border 206 of the torso 202. It is also a preferred feature of the invention that the anterior/posterior intersection 32 does not substantially extend posteriorly past the X-Z plane on the opposite side of the user and, more preferably, that anterior/posterior intersection 32 does not substantially extend posteriorly past the Y-Z plane at the center of the user 200.

Although the method for mounting the shoulder stabilizing restraint 10 on the user 200 has been disclosed above as a plurality of steps in a given sequence, the method of the present invention is not limited to any one particular sequence of the plurality of steps. It is apparent to the skilled artisan that the plurality of steps in the present method may be performed in accordance with any number of alternate sequences within the scope of the present invention.

Although not shown, the present embodiment of the shoulder stabilizing restraint 10 may be reconfigured to restrain and stabilize the left shoulder joint 208 of a user by disconnecting the shoulder strap 18 from the pillow 12 and waist belt 16 and disconnecting the forearm wrap 14 from the pillow 12. The pillow 12 and waist belt 16 are then flipped around to reverse their orientation. Accordingly, the top face 26 of the pillow 12 becomes the bottom face 26 and the bottom face 28 of the pillow 12 becomes the top face 28.

The mounting method is performed by reconnecting the shoulder strap 18 to the reversed pillow 12 and waist belt 16 and reconnecting the forearm wrap 14 to the reversed pillow 12. In particular, the connective segment 84 is releasably fastened to the reversed waist belt 16 and the second fastener 62 is releasably fastened to the bottom face 26 of the reversed pillow 12. The pillow 12 is positioned at the torso 202 of the user with the couplers 70, 72 of the waist belt 16 uncoupled and the forearm wrap 14 and shoulder strap 18 partially connected to the pillow 12. The posterior face 20 of the pillow 12 is fitted in essentially continuous engagement with the left anterior quadrant of the torso 202. As such, the posterior/lateral convergence 30 of the pillow rests adjacent to the left lateral border of the torso 202 and the plane of the lateral face 22 is in approximate perpendicular alignment with a plane including the left lateral border of the torso 202 and the central longitudinal axis of the torso 202. The shoulder strap 18 is draped over the right shoulder 226 of the user 200 with the shoulder segment 80 engaging the right shoulder 226 and the anterior segment 78 extending toward the second pillow connective loop.

The left hand of the user 200 is slipped through the hand support loop 104. The inside face of the left forearm of the user 200 is positioned in essentially continuous engagement with the lateral face 22 of the pillow 12 and the inside face of the left upper arm of the user 200 is positioned in engagement with, or in very close proximity to, the torso 202 proximal to left lateral border of the torso 202. The forearm wrap 14 is drawn upward so that the inside face 50 of the forearm wrap 14 engages the outside face of the left forearm. The first fastener 58 of the forearm wrap 14 is releasably fastened to the top face 28 of the pillow 12 retaining the left forearm in the forearm passageway 64 of the forearm wrap 14 and placing the left arm and left shoulder joint in the neutral position. The couplers 70, 72 of the waist belt 16 are coupled together and the length of the waist belt 16 is adjusted as necessary. Finally, the anterior segment 78 is connected to the pillow 12 by means of the second pillow connective loop. The length of the anterior segment 78 is adjusted such that the top and bottom faces 28, 26 of the pillow 12 are essentially horizontally aligned. The shoulder stabilizing restraint 10 retains the left arm and left shoulder joint in the neutral position thereafter.

While the forgoing preferred embodiments of the invention have been described and shown, it is understood that alternatives and modifications, such as those suggested and others, may be made thereto and fall within the scope of the invention. For example, it is alternatively within the scope of the present invention to place the forearm 214 in engagement with the top face 26 of the pillow 12 rather than with the lateral face 22 and maintain engagement of the forearm 214 with the top face 26 by securing the forearm wrap 14 onto the top face 26 over the forearm 214 in a manner readily apparent to the skilled artisan.

I claim:

1. A shoulder stabilizing restraint comprising:
   a pillow having a top face, a bottom face, an essentially linear lateral face connecting said top and bottom faces, an essentially arcuate posterior face having a length of about 90° or less for engaging an anterior quadrant of a torso on a first user side, and an anterior face connecting said lateral and posterior faces, wherein said posterior and lateral faces diverge anteriorly and converge posteriorly at a posterior/lateral convergence, said lateral face and said anterior face converge at a lateral/anterior intersection, said anterior face and said posterior face converge at an anterior/posterior intersection, said top face and said lateral face converge at a top/lateral intersection, and said bottom face and said lateral face converge at a bottom/lateral intersection;
   a forearm wrap having a first edge connectable to said top face of said pillow proximal to said top/lateral intersection and a second edge connectable to said bottom face of said pillow proximal to said bottom/lateral intersection to provide a forearm passageway having a first passageway side and a second passageway side for engaging a forearm on the first user side, wherein said forearm passageway is bounded on said first passageway side by said forearm wrap and on said second passageway side by said lateral face.

2. The shoulder stabilizing restraint of claim 1 wherein said posterior face is sized relative to the first user side so as not to extend substantially rearward past the anterior quadrant of the torso.

3. The shoulder stabilizing restraint of claim 1 wherein the forearm has a forearm length and said lateral face is sized relative to the first user side so as to approximate the forearm length.

4. The shoulder stabilizing restraint of claim 1 further comprising a shoulder strap connectable to said pillow.

5. The shoulder stabilizing restraint of claim 1 wherein said pillow has a unitary construction from a cushion material.

6. A shoulder stabilizing restraint comprising:
   a pillow having a top face, a bottom face, an essentially linear lateral face connecting said top and bottom faces an essentially arcuate posterior face having a length of about 90° or less for engaging an anterior quadrant of a torso on a first user side, and an anterior face connecting said lateral and posterior faces, wherein said posterior and lateral faces diverge anteriorly and converge posteriorly at a posterior/lateral convergence said lateral face and said anterior face converge at a lateral/anterior intersection, said anterior face and said posterior face converge at an anterior/posterior intersection, said top face and said lateral face converge at a top/lateral intersection, and said bottom face and said lateral face converge at a bottom/lateral intersection;
   a forearm wrap having a first edge connectable to said top face of said pillow proximal to said top/lateral intersection and a second edge connectable to said bottom face of said pillow proximal to said bottom/lateral intersection to provide a forearm passageway having a first passageway side and a second passageway side for engaging a forearm on the first user side, wherein said forearm passageway is bounded on said first passageway side by said forearm wrap and on said second passageway side by said lateral face, and wherein said forearm wrap is sized relative to the forearm to at least partially wrap around the forearm and retain the forearm within said forearm passageway.

7. A shoulder stabilizing restraint comprising:

a pillow having a top face, a bottom face, an essentially linear lateral face connecting said top and bottom faces, an essentially arcuate posterior face having a length of about 90° or less for engaging an anterior quadrant of a torso on a first user side, and an anterior face connecting said lateral and posterior faces, wherein said posterior and lateral faces diverge anteriorly and converge posteriorly at a posterior/lateral convergence, said lateral face and said anterior face converge at a lateral/anterior intersection, said anterior face and said posterior face converge at an anterior/posterior intersection, said top face and said lateral face converge at a top/lateral intersection, and said bottom face and said lateral face converge at a bottom/lateral intersection;

a forearm wrap having a first edge connectable to said top face of said pillow proximal to said top/lateral intersection, a first fastener positioned at said first edge for fastening said first edge to said pillow proximal to said top/lateral intersection, a second edge connectable to said bottom face of said pillow proximal to said bottom/lateral intersection, and a second fastener positioned at said second edge for fastening said second edge to said pillow proximal to said bottom/lateral intersection to provide a forearm passageway having a first passageway side and a second passageway side for engaging a forearm on the first user side, wherein said forearm passageway is bounded on said first passageway side by said forearm wrap and on said second passageway side by said lateral face.

8. The shoulder stabilizing restraint of claim 7 wherein said first fastener of said forearm wrap is a hook and loop fastener extending along said first edge and said second fastener of said forearm wrap is a hook and loop fastener extending along said second edge.

9. A shoulder stabilizing restraint comprising:

a pillow having a top face, a bottom face, an essentially linear lateral face connecting said top and bottom faces, an essentially arcuate posterior face having a length of about 90° or less for engaging an anterior quadrant of a torso on a first user side, and an anterior face connecting said lateral and posterior faces, wherein said posterior and lateral faces diverge anteriorly and converge posteriorly at a posterior/lateral convergence, said lateral face and said anterior face converge at a lateral/anterior intersection, said anterior face and said posterior face converge at an anterior/posterior intersection, said top face and said lateral face converge at a top/lateral intersection, and said bottom face and said lateral face converge at a bottom/lateral intersection, and wherein said lateral, posterior, and anterior faces of said pillow are essentially vertically aligned and define an essentially triangular profile of said pillow;

a waist belt connected to said pillow;

a shoulder strap having a first end releasably connected to said pillow proximal to said lateral/anterior intersection and a second end connected to said waist belt;

a forearm wrap having a first edge connectable to said top face of said pillow proximal to said top/lateral intersection and a second edge connectable to said bottom face of said pillow proximal to said bottom/lateral intersection to provide a forearm passageway having a first passageway side and a second passageway side for engaging a forearm on the first user side, wherein said forearm passageway is bounded on said first passageway side by said forearm wrap and on said second passageway side by said lateral face.

10. A shoulder stabilizing restraint comprising:

a pillow having a top face, a bottom face, an essentially linear lateral face connecting said top and bottom faces, an essentially arcuate posterior face having a length of about 90° or less for engaging an anterior quadrant of a torso on a first user side, and an anterior face connecting said lateral and posterior faces, wherein said posterior and lateral faces diverge anteriorly and converge posteriorly at a posterior/lateral convergence, said lateral face and said anterior face converge at a lateral/anterior intersection, said anterior face and said posterior face converge at an anterior/posterior intersection, said top face and said lateral face converge at a top/lateral intersection, and said bottom face and said lateral face converge at a bottom/lateral intersection, and wherein said lateral, posterior, and anterior faces of said pillow are essentially vertically aligned and define an essentially triangular profile of said pillow;

a waist belt connected to said pillow;

a shoulder strap having a first end and a second end;

a first releasable strap connector on said top face of said pillow proximal to said lateral/anterior intersection releasably connecting said first end of said shoulder strap to said pillow proximal to said lateral/anterior intersection, said second end of said shoulder strap connected to said waist belt;

a forearm wrap having a first edge connectable to said top face of said pillow proximal to said top/lateral intersection and a second edge connectable to said bottom face of said pillow proximal to said bottom/lateral intersection to provide a forearm passageway having a first passageway side and a second passageway side for engaging a forearm on the first user side, wherein said forearm passageway is bounded on said first passageway side by said forearm wrap and on said second passageway side by said lateral face.

11. The shoulder stabilizing restraint of claim 10, further comprising a second releasable strap connector on said bottom face of said pillow proximal to said lateral/anterior intersection for releasably connecting said first end of said shoulder strap to said pillow when said pillow is reversed to engage a forearm on a second user side and an anterior quadrant of the torso on the second user side.

12. A method for restraining a shoulder joint on a first side of a torso of a user, wherein said shoulder joint is connected to an arm having an upper arm, an elbow joint, and a forearm, said method comprising:

providing a pillow having a top face, a bottom face, a posterior face, a lateral face connecting said top and bottom faces, and an anterior face connecting said lateral and posterior faces, wherein said posterior face and said lateral face diverge anteriorly and converge posteriorly at a posterior/lateral convergence, said lateral face and said anterior face converge at a lateral/anterior intersection, said anterior face and said posterior face converge at an anterior/posterior intersection, said top face and said lateral face converge at a top/ lateral intersection, and said bottom face and said lateral face converge at a bottom/lateral intersection;

positioning said pillow to engage said posterior face with an anterior quadrant of said torso on said first side of said user and to engage said lateral face with said forearm:

positioning said posterior/lateral convergence adjacent to said torso on said first side of said user;

fixing said position of said pillow relative to said user by encircling said torso with a waist belt connected to said pillow and extending a shoulder strap having a first end connected to said pillow over a shoulder on an opposite side of said user and connecting a second end of said shoulder strap to said waist belt while maintaining said shoulder strap substantially free of engagement with said pillow or said forearm wrap, thereby maintaining said forearm in engagement with said lateral face and said shoulder joint at a positive external rotation angle; and wrapping a forearm wrap over said forearm and connecting a first edge of said forearm wrap to said pillow proximal to said top/lateral intersection and connecting a second edge of said forearm wrap to said pillow proximal to said bottom/lateral intersection to engage said forearm with said forearm wrap while maintaining said forearm in engagement with said lateral face.

13. The method of claim 12 wherein said first edge of said forearm wrap is connected to said top face of said pillow and said second edge of said forearm wrap is connected to said bottom face of said pillow.

* * * * *